United States Patent [19]
Shelden et al.

[11] Patent Number: 5,473,082
[45] Date of Patent: Dec. 5, 1995

[54] DEVICE FOR CARRYING OUT CATALYZED REACTIONS

[75] Inventors: Ronald Shelden, Winterthur; Jean-Paul Stringaro, Bulach, both of Switzerland

[73] Assignee: Sulzer Brothers Limited, Winterthur, Switzerland

[21] Appl. No.: 92,504

[22] Filed: Jul. 15, 1993

Related U.S. Application Data

[62] Division of Ser. No. 499,367, May 31, 1990 filed as PCT/CH89/00150, Aug. 22, 1989.

[30] Foreign Application Priority Data

Sep. 2, 1988 [CH] Switzerland ............... 93285/88
Feb. 17, 1989 [CH] Switzerland ............... 00577/89

[51] Int. Cl.⁶ ............................................. C07D 249/16
[52] U.S. Cl. .................... 549/258; 549/259; 422/197; 422/211
[58] Field of Search ...................... 422/197, 211; 549/248, 259, 260, 258

[56] References Cited

U.S. PATENT DOCUMENTS

| | | | |
|---|---|---|---|
| 2,773,838 | 12/1956 | Reid et al. | 549/259 |
| 2,773,921 | 12/1956 | Rylander eet al. | 585/466 |
| 3,106,569 | 10/1963 | Robinson | 549/248 |
| 3,293,268 | 12/1966 | Bergman et al. | 549/259 |
| 3,755,535 | 9/1971 | Naber | 55/387 |
| 3,904,652 | 9/1975 | Frank | 549/260 |
| 4,005,017 | 1/1977 | Kusano et al. | 210/284 |
| 4,044,027 | 8/1977 | Anderson et al. | 549/259 |
| 5,011,945 | 4/1991 | Taheri | 549/260 |

*Primary Examiner*—Timothy M. McMahon
*Attorney, Agent, or Firm*—McAulay Fisher Nissen Goldberg & Kiel

[57] ABSTRACT

The catalytic process for producing maleic anhydride employs a catalytic device formed of pairs of vertically extending vapor permeable walls which define flow channels between the pairs of walls. In addition, each pair of walls defines an interspace which contains a catalyst. A mixture of air and n-butane is passed through the flow channels while a heat exchange medium, such as a molten salt, is passed in heat exchange relation to the catalytic device while effecting an exothermic catalytic reaction of the mixture within the catalytic device. The resulting gaseous maleic anhydride is produced as a product.

6 Claims, 7 Drawing Sheets

DEVICE FOR CARRYING OUT CATALYZED REACTIONS

This is a division of application Ser. No. 499,367 filed May 31, 1990 filed as PCT/CH89/00150, Aug. 22, 1989.

The invention relates to a device for carrying out catalyzed reactions and to the use of devices of this kind.

Catalytic solid bed reactors represent an important field of use of the invention, for example for oxidation or hydrogenation reactions.

The reaction space of known embodiments of reactors of this kind contains fills of solid catalyst particulates which are spherical or pellet-shaped, for example, and around which the reactants flow.

On the one hand, considerable pressure drops occur in reactors of this kind, while on the other there is no homogeneous temperature distribution over the reactor cross section. A further disadvantage lies in the fact that there is no uniform concentration distribution over the reactor cross section, so that the required end product yield is not as high as it could be.

Finally, a considerable number of the usual chemical reactions are exothermic and thus give rise to local overheating in the reactor bed (so-called hot spots). This limits the useful life of the catalyst materials and reduces selectivity, particularly in oxidation reactions.

In order to limit the effects of the local overheating occurring in this case, i.e. to improve the conduction of heat to the reactor walls, a number of tubes with catalyst fills, around which a heat-absorbing medium flows, are usually arranged in the reaction space. However an embodiment of this kind is extremely expensive to operate and produce.

If the layers of the actual devices are to be formed from catalyst material, this depends on the possibility of shaping the material as required in a simple manner. Materials of this kind may also be very expensive.

The object of the invention is to provide a device which permits advantageous utilization of the catalyst materials and a long useful life when carrying out catalyzed reactions and allows a wide range of catalyst materials to be used.

Briefly, the invention provides a device for catalyzed reactions comprising a plurality of layers disposed in parallel relation with flow channels between the layers for reactants and with each layer defining an interspace therein. In addition, a catalyst material is disposed in each interspace of each layer. Further, each layer is made of a material impermeable to the catalyst material and permeable to the reactants to permit a catalyzed reaction to occur in a respective interspace.

In one embodiment, a plurality of guide elements space the layers from each other while at the same time defining the flow channels. In this embodiment, each layer has a pair of flat parallel walls defining a pocket-like interspace.

In another embodiment, each layer has a pair of corrugated walls defining a respective interspace with at least some of the walls being in contact with an adjacent wall of an adjacent layer to define the flow channels.

In the embodiment employing guide elements, the respective elements may be in the form of a corrugated plate, a rod element, and/or a plate disposed perpendicular to and between a pair of adjacent layers.

In either embodiment, each layer may be made of one of wire cloth and knitted wire fabric. Alternatively, each layer may be made of a material selected from the group consisting of metal, glass and plastic. Also, each layer may be made of non-woven plastic or non-woven glass fibers. Still further, each layer may be made of a porous material, a semipermeable membrane or a sintered material.

The catalyst material may be selected from the group consisting of solid particles, liquids including materials dissolved in a liquid and gases. Still further, the catalyst material may be a polymerized solid or may be a porous ceramic or a sintered structure.

The devices for catalyzed reactions may be used in a catalytic reactor as well as a catalytic rectifying column.

In the case of a catalytic reactor having a housing with an admission space for reactants and a delivery space for drawing off reactant product, a plurality of tubes are disposed to connect the two spaces with each other while a plurality of the catalyzed reaction devices are disposed in each tube for a catalyzed reaction therein. The reactor may also be provided with a suitable tube connection in the housing for supplying a heat conveying medium to a heat exchange space about the tube while a tube connection is provided in the housing for removing the medium from the heat exchange space.

In the case of a catalytic rectifying column, a catalytic solid bed reactor is provided with a plurality of devices of the above type for a catalyzed reaction. In addition, a mass transfer section is disposed both above and below the reactor. Also, a drain can be provided below the lower mass transfer section to remove a liquid product while a line is disposed above the other mass transfer to remove gaseous product.

This object is solved according to the invention by the features of claim 1. The dependent claims relate to particularly advantageous embodiments of the invention.

A uniform temperature distribution, concentration equalization over the cross section, limited residence time and very little, if any, back mixing are essential advantages of the invention. The uniform temperature equalization and the favourable heat transfer to the reactor walls are in particular decisive for a long useful life of the catalyst materials and for a high product yield and selectivity. This effect is particularly important in exothermic reactions, as heat resulting from these can be more quickly conducted away from overheated spots to the reactor walls. This also results in improved operating safety (no runaway).

Also of considerable importance is the fact that, due to the uniform temperature distribution and the concentration equalization over the reactor cross section, the desired reaction product can be obtained in large quantities and with a high quality and there is only a relatively small quantity of non-reacted educts.

A further essential advantage of the invention lies in the fact that it also utilizes the properties which are known per se for pure mixing processes, such as, e.g. uniform temperature distribution and concentration equalization over the cross section, limited residence time and very little, if any, back mixing.

The solid bed reactors fitted with devices according to the invention can be formed with a substantially smaller number of individual tubes than known solid bed reactors, with the same flow rate. A single device according to the invention may be sufficient for a solid bed reactor, i.e. in this case the cross section of the device corresponds to that of the reactor housing.

It may also be advantageous to arrange a plurality of devices of this kind above one another in the reactor housing, with the superimposed devices advantageously being staggered in relation to the longitudinal axis of the reactor by approximately 90°.

So-called catalytic distillation processes, which essentially consist of a combination of a catalyzed reaction and a distillation or rectification process, represent an advantageous field of application of the devices of the invention.

Processes of this kind and various applications are described in detail, for example, in an article entitled "CATALYTIC DISTILLATION, Combining chemical reaction with product separation" by William P. Stadig, Houston Regional Editor of the journal "Chemical Processing", February 1987.

The known rectifying columns comprise at least one solid bed reactor and mass transfer zones, in which the products resulting from the reaction are separated from the non-reacted educts and any undesirable by-products. The rectification is a continuous process and therefore also takes place in the catalytic zone in addition to the catalyzed reaction, preferably at the boiling temperature of the product to be obtained, with the boiling temperature being regulated by adjusting the column pressure accordingly. Details relating to the way in which a combined process of this kind is carried out are found in the above-mentioned article.

So-called coiled bodies are arranged in the catalytic reaction zone in the known process. These coiled bodies, which serve to hold a solid catalyst material, consist of a wound wire cloth strip of stainless steel, by means of which a layer consisting of glass fibres and containing corrosive catalyst particles is secured. The advantage of this embodiment lies in the fact that the column wall can be made of a corrosive material, such as carboniferous steel, which does not come into contact with the catalyst material.

In contrast with the static mixer structures arranged according to the invention, a considerable disadvantage of these coiled bodies lies in the fact that there is no radial temperature and concentration equalization over the column cross section and, moreover, due to the irregular flow form of the reactants or the products resulting from the reaction in addition to the by-products, there is a relatively substantial pressure drop, something which is not found in the regular static structures used according to the invention.

If the known coiled bodies in the catalytic reaction zone are replaced by the structures according to the invention, all the advantages provided by the catalytic solid bed reactor described above are achieved.

BRIEF DESCRIPTION OF THE DRAWINGS

The invention is explained in the following on the basis of embodiments illustrated diagrammatically in the drawings, in which.

Figure 1:
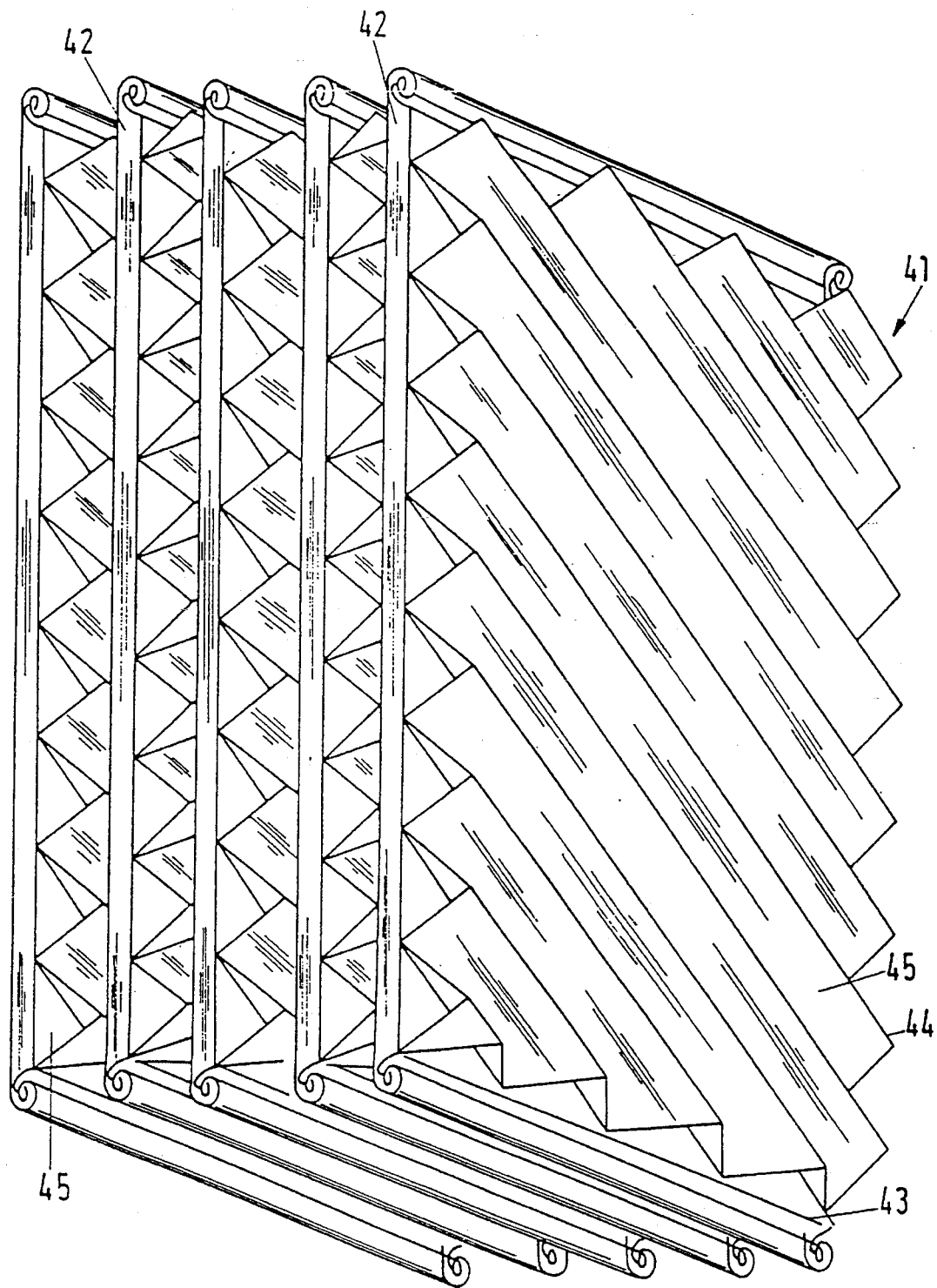
FIG. 1 is an example of a device formed according to the invention.
Figure 1A:
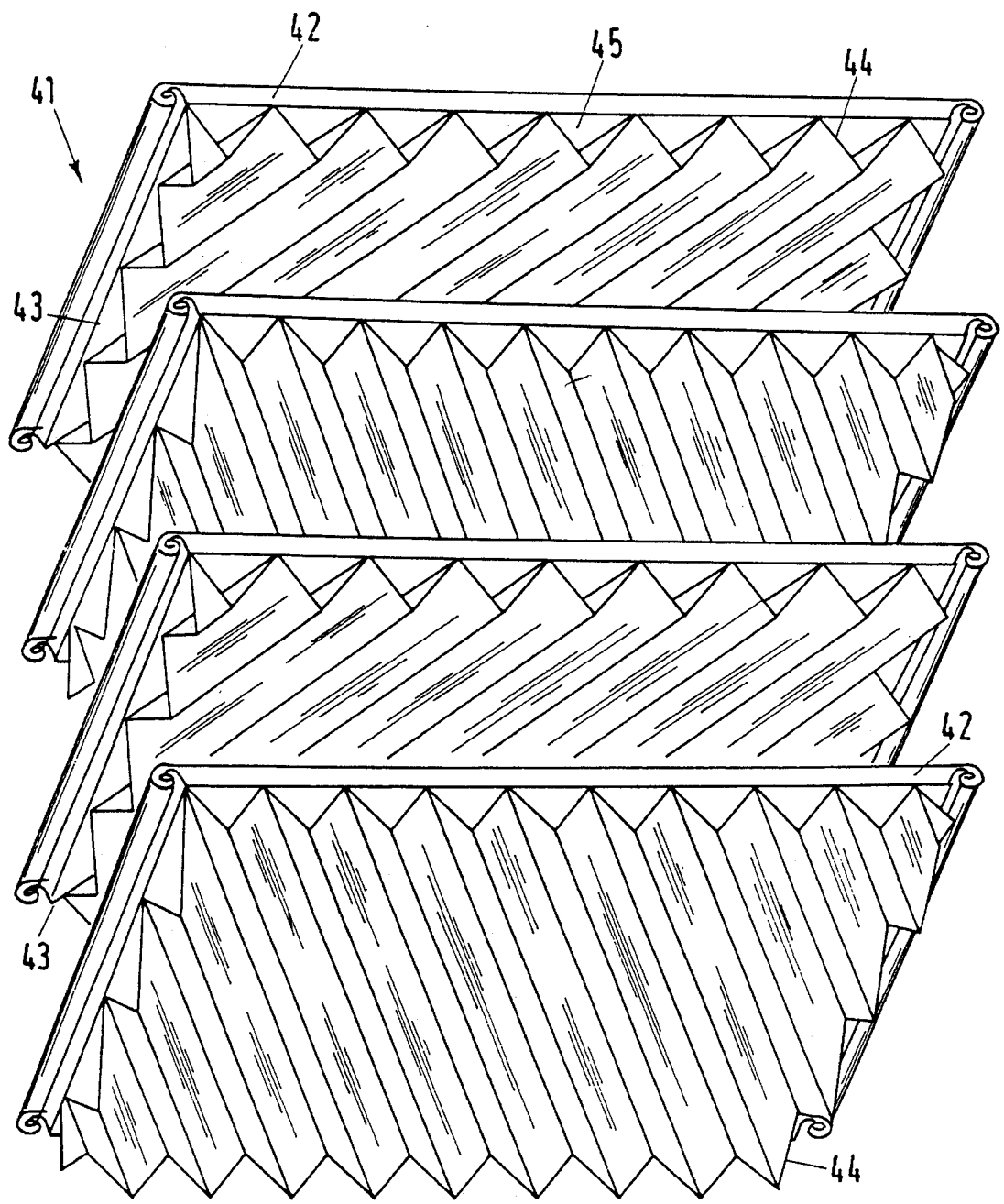
FIG. 1a is the example of FIG. 1 in a disassembled arrangement.

The device 41 shown in FIGS. 1 and 1a consists of pocket-like layers 42 which are arranged parallel to one another and are in each case connected at a side wall 43 to guide elements 44.

In the embodiment these guide elements consist of corrugated sheet metal plates, with the crests and troughs forming side walls of the flow channels 45 for the reactants.

Figure 1B:
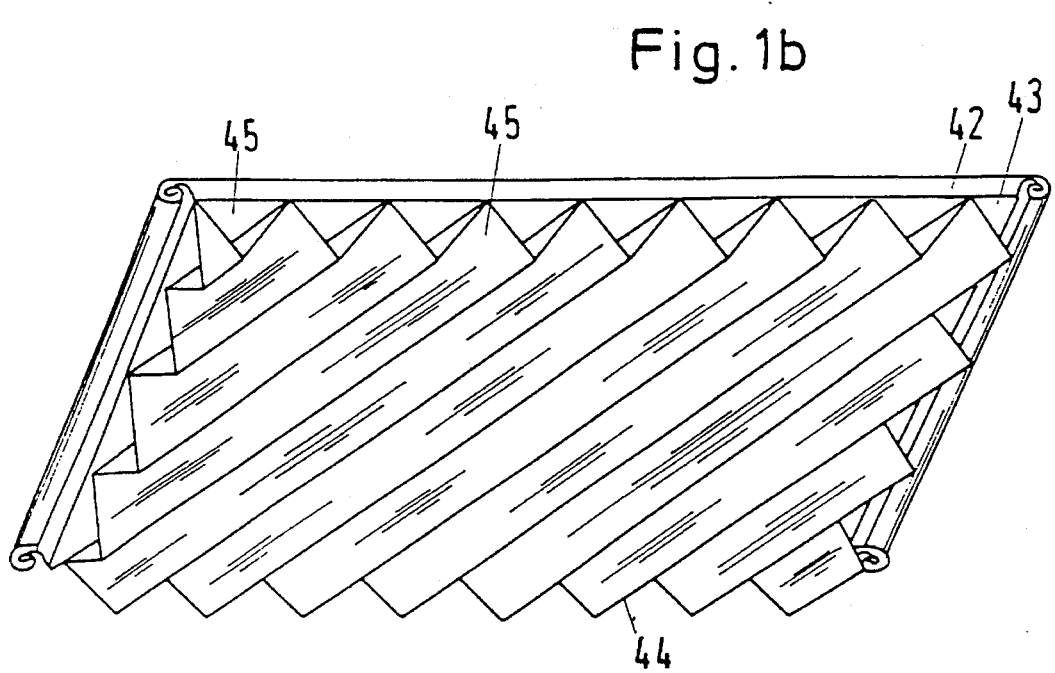
FIGS. 1b and 1c are each perspective views of pocket-like layers.
Figure 1C:
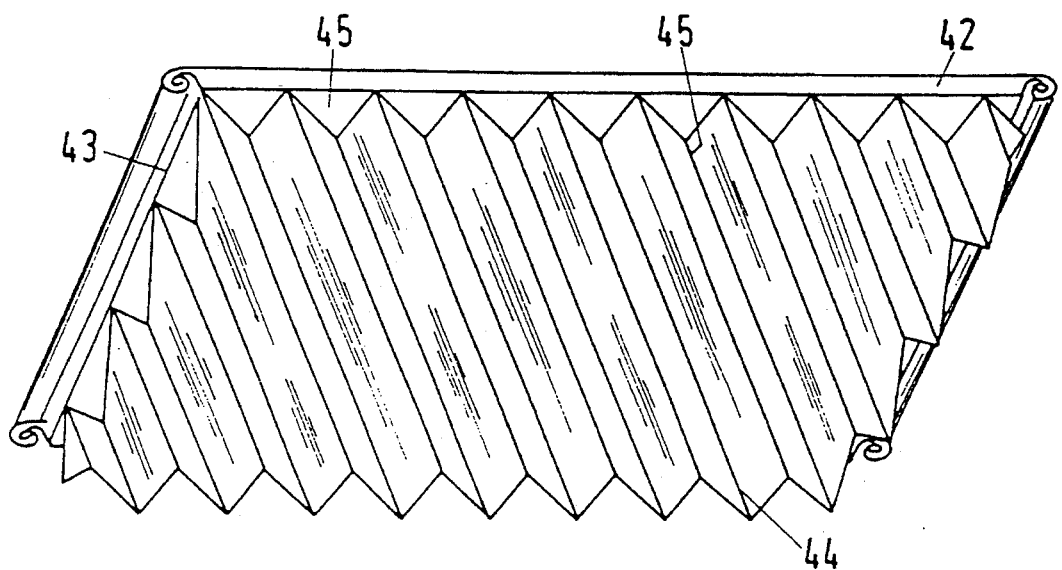

It is advantageous to form these corrugated sheet metal plates such that the flow channels which they produce form an angle with respect to the longitudinal axis of the pockets 42 (cf. FIGS. 1b and 1c).

Adjacent layers are then joined when a reactor 41 is assembled such that the flow channels 45 of adjacent layers 42 intersect. This permits excellent radial cross mixing of the component flows of the reactants in the manner of a static mixer, in particular in the case of a plurality of devices 41 which are arranged one after the other and preferably staggered by approximately 90°.

The guide elements 44 simultaneously serve to reinforce layer 42, which is connected to them by, for example, spot welding. Their crests contact the side wall of the adjacent layer 42 without guide elements and thus simultaneously serve as a spacing means. It should be mentioned that the term "corrugated" also covers zigzag profiling of the plate.

As in the embodiment, the guide elements 44 may, for example, consist of sheet metal, perforated sheet metal, plastic or a wire cloth or similar.

The side walls 43 of the pocket-like layers 42, which are firmly connected together at their side edges, e.g. by rivet, weld or soldered joints, consist of a material which is permeable to the reactants and impermeable to the catalyst material.

A solid, liquid or gaseous catalyst material 48, which is chosen in accordance with the intended purpose, is placed in the pockets of the layers 42.

It is also possible to fill the interspaces with a pourable catalyst material which is mixed with a plastic base and then to polymerize the mixture so as to produce a porous material mass which is permeable to the reactants.

Another possibility lies in filling the interspaces with a pourable catalyst material and then forming a porous ceramic or sintered structure from this by treating it accordingly.

The device 41 may have a circular cross section. The shape of the cross section is adapted to that selected for the reactor housing, i.e. the device 41 may, for example, also be square, rectangular or polygonal.

Figure 2A:
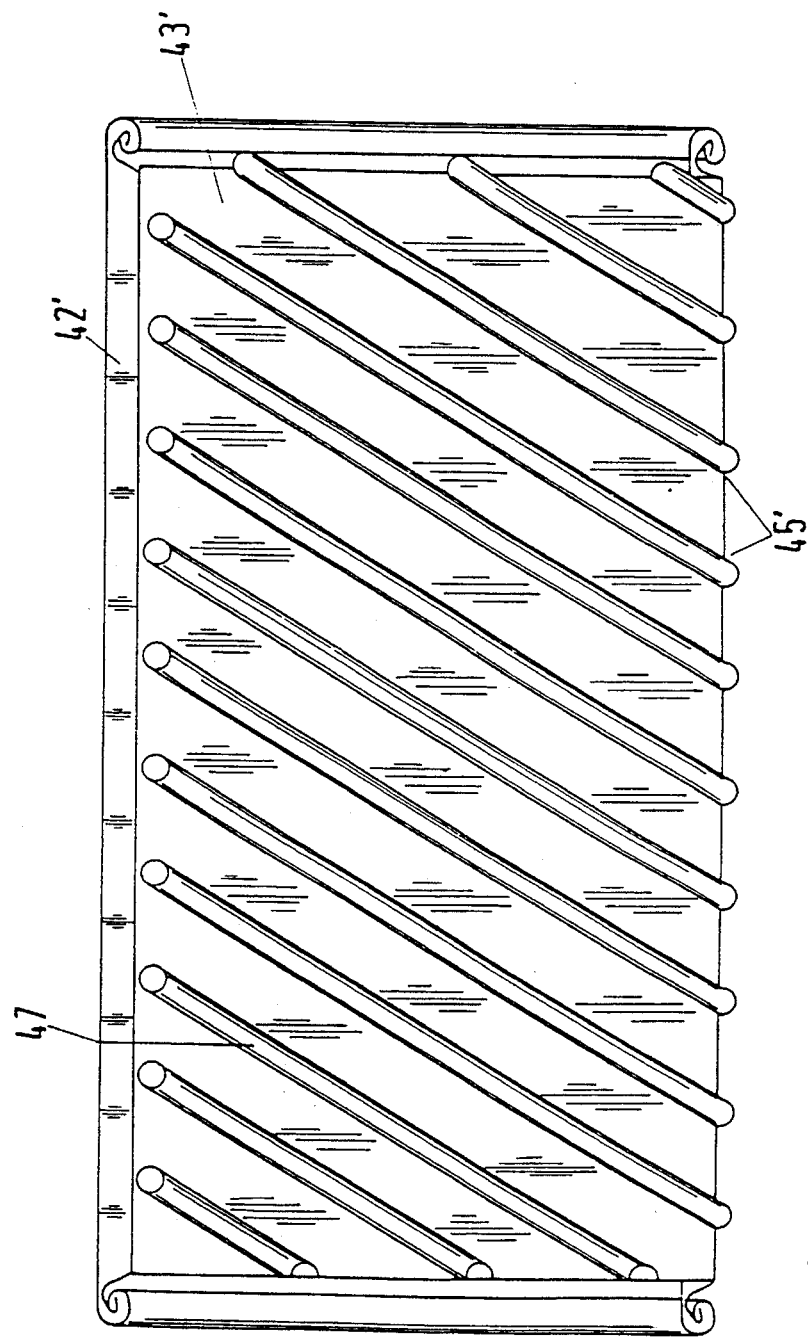
FIGS. 2a and 2b are side and plan views, respectively, of a variant.
Figure 2B:
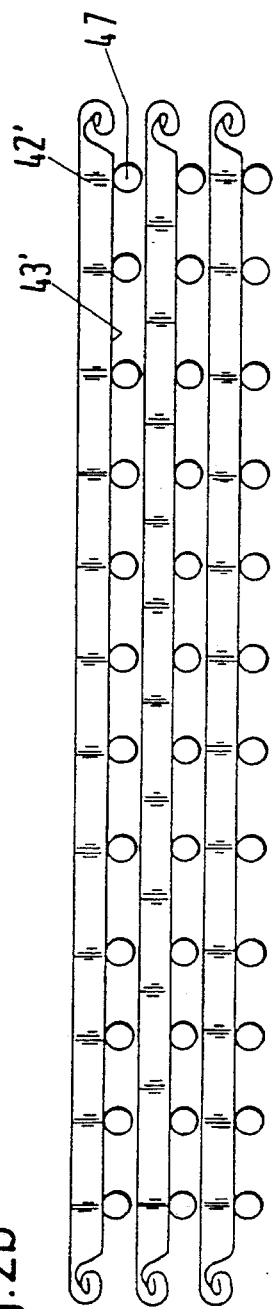

In the embodiment illustrated in FIGS. 2a and 2b, the guide elements of the layers 42' are formed as rod elements 47 and connected to the pocket walls 43', e.g. by spot welding. Otherwise all the above information relating to the example illustrated in FIGS. 1, 1a, 1b and 1c applies.

Figure 3:
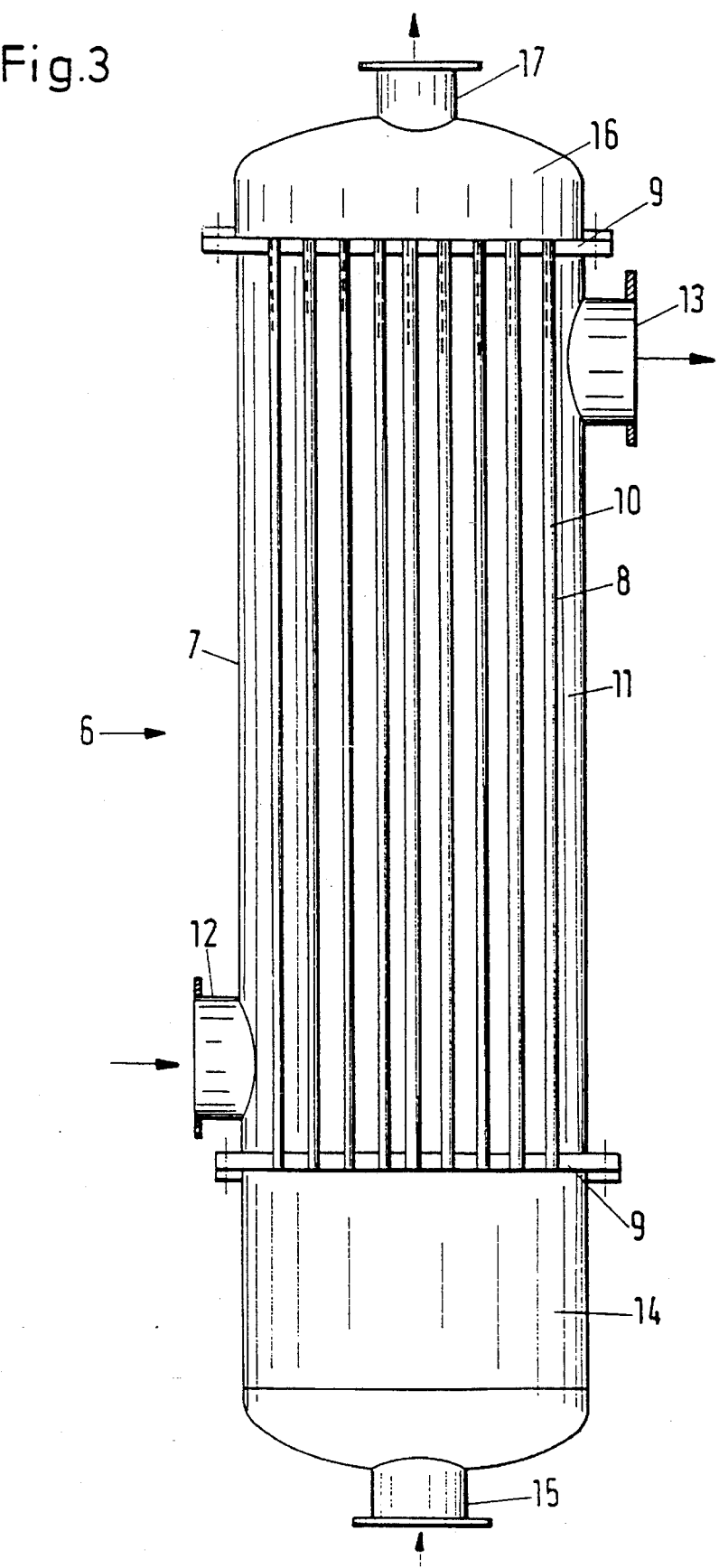
FIG. 3 is a catalytic solid bed reactor.

FIG. 3 is a diagrammatic representation of a catalytic solid bed reactor 8 with a cylindrical housing 7. Tubes 8, the open ends of which are secured in tube plates 9, are arranged in the housing 7.

Devices 10, which are formed according to the invention, are arranged above one another in the tubes 8, with adjacent devices in each case being staggered by an angle of 90° with respect to the tube axis when they are formed as the embodiments illustrated in FIGS. 1, 1a–1c and 2a and 2b.

Tube connections 12 and 13 adjoin the heat exchange space 11 to supply and remove a heat-supplying and heat-removing medium, e.g. a molten salt, which flows around the tubes 8.

An admission space 14 for the reactants supplied through a connection sleeve 15 is arranged below the reaction tubes 8 and a delivery space 18 for carrying away the product and the by-products is arranged above the reaction tubes 8.

In an example of a catalyzed reaction, a mixture of air and n-butane is fed through the connection sleeve 15 and the admission space 14 into the tubes 8 at a temperature of, for example, 200°–800° C., in which case the reaction can be carried out at approximately 1 bar.

Phosphorus pentoxide and vanadium pentoxide may be used as catalysts in this case.

The reaction is exothermic and the heat produced is absorbed by a molten salt, for example, which flows over the reaction tubes 8. The heated molten mass is removed in a manner which is not shown through the outlet 18, cooled to the required temperature and recirculated through the inlet 12 into the heat exchange space 11.

In the present case, the product obtained is gaseous maleic anhydride, which is fed from the reactor 6 through the outlet 17 to a further processing stage. This is because the product is not obtained in a pure form, being mixed with educts, in the present case n-butane or by-products resulting from the formation of maleic anhydride, such as oxygen, water, maleic acid, carbon monoxide and carbon dioxide.

The further processing may take place in a manner which is known per se, for example in distillation processes.

Due to the use of the devices formed according to the invention and their advantages described above, substantially less tubes are required than in the known reactor described in the introduction. Overheating is at least largely prevented due to the good heat transfer through the tube walls, so that, as compared with the known embodiment, only relatively small amounts of carbon monoxide, carbon dioxide and water, which reduce the selectivity and activity of the catalyst, are formed.

Also possible are embodiments of a catalytic solid bed reactor consisting of only one tube, in which at least one device according to the invention is arranged.

Figure 4:
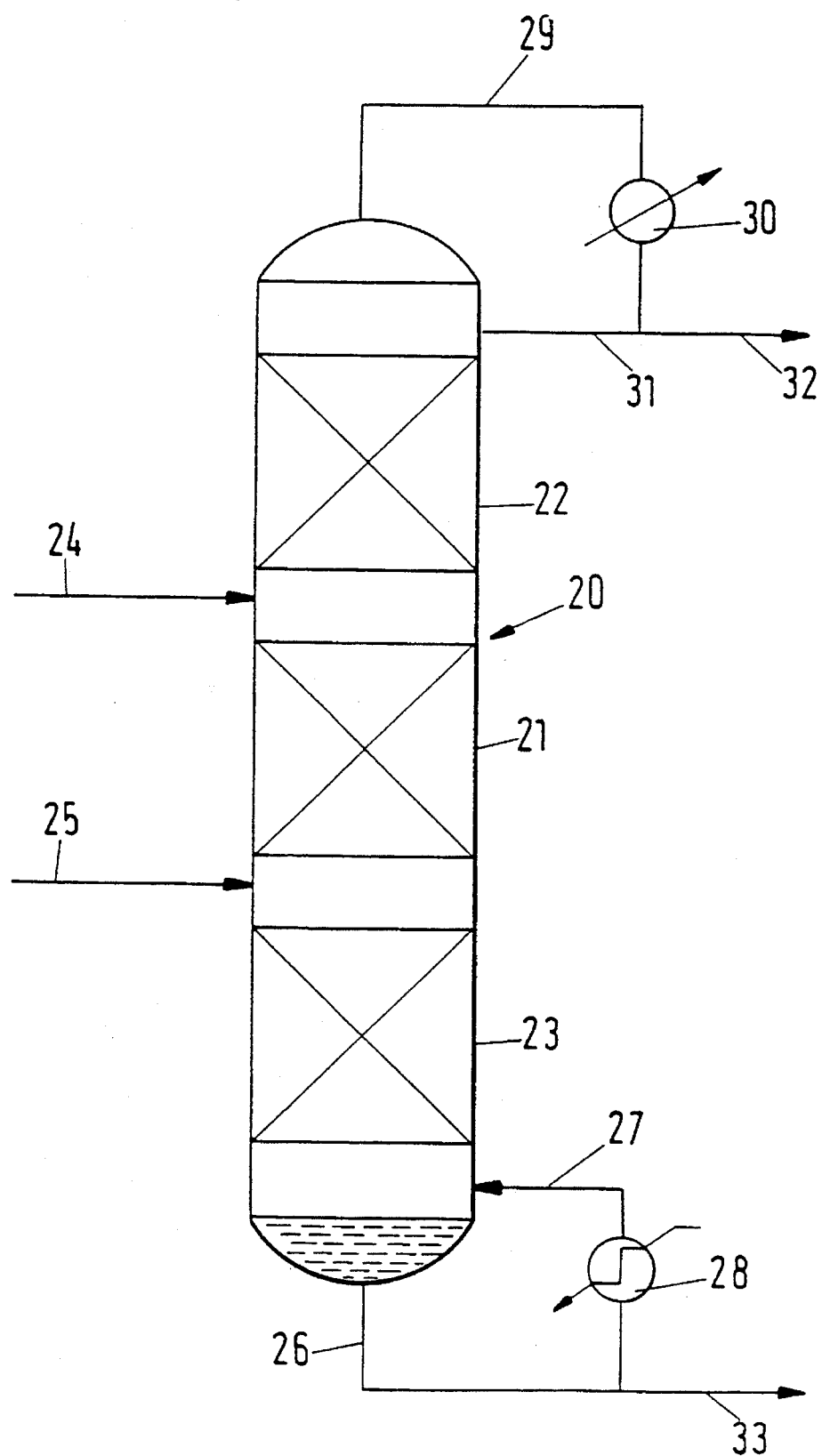
FIG. 4 is a rectifying column for carrying out a combined process.

FIG. 4 is a diagrammatic representation of a catalytic rectifying column 20, in which a catalytic solid bed reactor section 21, which is provided with devices formed according to the invention (see, e.g., FIG. 1), is arranged.

Mass transfer sections 22 and 23 are arranged above and below this solid bed reactor section 21. The mass transfer of the products resulting in the section 21 takes place in the sections 22 and 23. These sections may be formed in a known manner as, for example, sieve or bubble-cap plates. Liquid and gaseous or vaporous phases may pass through the packing material in counter-flow. The individual folded layers may also be formed as single layers, i.e. they do not have double walls with interspaces.

Apart from the reaction taking place in the solid catalyst bed 21 between the reactants fed in through the lines 24 and 25, the reaction mixture is also rectified in this section.

A drain 26 for the liquid bottom product is connected to the bottom of the column. Some of this product is recirculated in a manner which is known per se through a line 27 into the column 20 following vaporization in a vaporizer 28.

A line 29 for removing the gaseous or vaporous head product is also connected in a known manner to the head of the column 20. After this head product has been liquefied in a condenser 30, some of it is returned to the column as reflux through a line 31, while the remaining quantity of liquid is removed from the rectification process via a line 32.

The advantages of the solid bed section 21 formed according to the invention are the same as those of the embodiment illustrated in FIG. 3.

As the rectifying column 20 is operated at the boiling temperature of the product resulting from the reaction, there are of course no overheated spots, as the heat resulting from an exothermic reaction causes the liquid phase to vaporize. However in this case this is an important advantage from the energy aspect because of the necessary low capacity of the vaporizer 28.

The use of the invention also enables plant of this kind to be scaled up on the basis of the above-mentioned advantages.

The solid catalyst, section 21 is arranged in the central, lower or upper part of the column, according to the process. The object of the embodiment in question is to obtain 3-methyl butyl ether from methanol and a mixture of saturated and unsaturated 4 carbon-chain hydrocarbons.

Acidic ion exchange resins, for example, may be used as the catalyst material in the section 21.

The reactant consisting of methanol is fed into the column 20 through the line 24 above the section 21, while the reactant consisting of a mixture of saturated and unsaturated 4 carbon-chain hydrocarbons is fed into the column 20 through the line 25 below the section 21.

Non-reacted 4 carbon-chain hydrocarbons are separated in counter-flow to the liquid phase from the reaction products in the mass transfer section 22, removed in the form of vapours at the head of the column 20, liquefied in the condenser 30 and returned in part to the column 20 as reflux. The remaining quantity may, for example, be returned as a reactant through the line 25 to the column 20.

The end product, which is obtained in liquid form and consists of 3-methyl butyl ether, is conveyed out of the column 20 at the bottom of the latter. Some is vaporized in the vaporizer 28 and recirculated into the column 20. The liquid end product is removed from the plant for further processing through a line 33.

Figure 5:
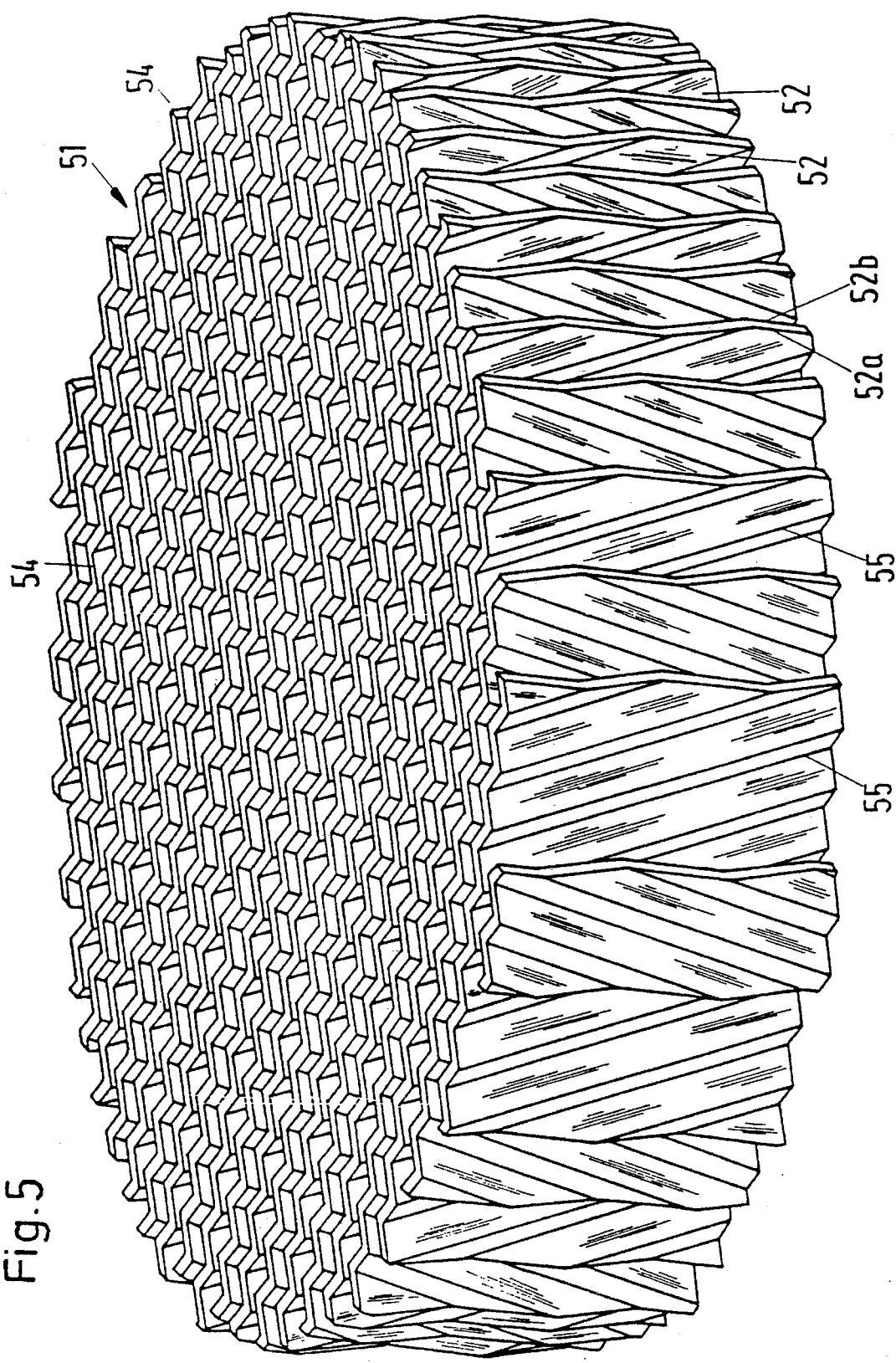
FIG. 5 is a perspective view of another embodiment of a device formed according to the invention.

The device 51 illustrated in FIG. 5 consists of folded layers 52 which are arranged parallel to one another and in each case consist of a double shell 52a and 52b, the walls consisting of a material which is permeable to the reactants and impermeable to the catalyst material.

A solid, liquid or gaseous catalyst material 54, which is chosen in accordance with the intended purpose, is introduced into the interspaces formed by the double walls 52a and 52b.

As above, it is also possible to fill the interspaces with pourable catalyst material which is mixed with a plastic base and then to polymerize the mixture so as to produce a porous material mass which is permeable to the reactants.

Another possibility lies in filling the interspaces with pourable catalyst material and then forming a porous ceramic or sintered structure from this by treating it accordingly.

In the embodiment illustrated the device 51 has a circular cross section. The shape of the cross section is adapted to that selected for the reactor housing, i.e. the device 51 may, for example, also be square, rectangular or polygonal.

The individual layers 52 are folded, with the folds 55 being at an angle to the longitudinal axis of the device and the folds of adjacent layers 52 intersecting.

The invention should thus be applicable to both solid catalyst material, such as platinum, metal oxides, zeolite or ion exchange resins, and catalytic solutions, such as aqueous palladium oxide and copper chloride solutions, or liquid catalyst materials, such as sulphuric or hydrochloric acid. The invention should also permit the use of gaseous catalyst material such as hydrogen chloride or hydrogen fluoride, for example.

We claim:

1. A process comprising the steps of directing a mixture of air and n-butane over a plurality of pairs of vertically extending vapor permeable walls disposed in spaced pairs to form flow channels between said pairs and having a catalyst disposed between each pair of walls within a catalyst reaction column;

directing a flowable heat-removing medium in heat exchange relation with the mixture of air and n-butane to effect a catalytic reaction of the mixture into gaseous maleic anhydride; and removing the gaseous maleic anhydride as a product.

2. A process as set forth in claim 1 wherein said flowable medium is molten salt.

3. A process as set forth in claim 1 wherein the catalyst includes phosphorus pentoxide and vanadium pentoxide.

4. A catalytic process comprising the steps of directing a heated mixture of air and n-butane into end through at least one tube having at least one catalytic device therein formed of a plurality of pairs of vertically extending vapor permeable walls defining flow channels between said pairs of walls and having a catalyst disposed between each pair of walls.

directing a heat exchange medium over said tube while effecting an exothermic catalytic reaction of the mixture therein into gaseous maleic anhydride; and removing the gaseous maleic anhydride from the tube.

5. A catalytic process as set forth in claim 4 wherein a corrugated guide element is disposed in each flow channel to effect a lateral mixing of the mixture of air and n-butane passing therethrough.

6. A catalytic process as set forth in claim 4 wherein each wall is corrugated.

* * * * *

UNITED STATES PATENT AND TRADEMARK OFFICE
CERTIFICATE OF CORRECTION

PATENT NO.    : 5,473,082

ISSUED        : December 5, 1995

INVENTOR(S)   : Ronald Shelden

It is certified that this error appears in the above-identified patent and that said Letters Patent is hereby corrected as shown below:

Column 2, line 24, after "transfer" insert --section--

Lines 26 to 28, cancel "this object ... invention."

Column 7, line 15, change "end" to "and"

Signed and Sealed this

Fourth Day of June, 1996

Attest:

BRUCE LEHMAN

Attesting Officer

Commissioner of Patents and Trademarks